United States Patent
Mukerjee et al.

(10) Patent No.: US 9,840,584 B2
(45) Date of Patent: *Dec. 12, 2017

(54) POLYESTER POLYOLS FROM THERMOPLASTIC POLYESTERS AND DIMER FATTY ACIDS

(71) Applicant: Resinate Materials Group, Inc., Plymouth, MI (US)

(72) Inventors: Shakti L Mukerjee, Canton, MI (US); Rick Tabor, Plymouth, MI (US); Adam William Emerson, Ypsilanti, MI (US); Kevin Anthony Rogers, Farmington, MI (US); Eric D Vrabel, Ferndale, MI (US); Matthew T Brown, Novi, MI (US); Matthew J Beatty, Ann Arbor, MI (US); Jack Rogers Kovsky, Livonia, MI (US); Michael D Kellerman, Ann Arbor, MI (US); Michael Robert Christy, Midland, MI (US)

(73) Assignee: Resinate Materials Group, Inc., Plymouth, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 14/822,528

(22) Filed: Aug. 10, 2015

(65) Prior Publication Data

US 2015/0344622 A1 Dec. 3, 2015

Related U.S. Application Data

(63) Continuation of application No. PCT/US2015/028644, filed on Apr. 30, 2015.

(60) Provisional application No. 61/988,866, filed on May 5, 2014, provisional application No. 62/074,819, filed on Nov. 4, 2014, provisional application No. 62/078,880, filed on Nov. 12, 2014.

(51) Int. Cl.

| | |
|---|---|
| *C08G 63/91* | (2006.01) |
| *C09D 175/06* | (2006.01) |
| *C08G 18/75* | (2006.01) |
| *C08G 18/73* | (2006.01) |
| *C08G 18/42* | (2006.01) |
| *C08J 11/24* | (2006.01) |
| *C08G 63/553* | (2006.01) |
| *C08G 18/36* | (2006.01) |
| *C07C 67/03* | (2006.01) |
| *C07C 67/08* | (2006.01) |
| *C07C 69/82* | (2006.01) |
| *C08G 101/00* | (2006.01) |

(52) U.S. Cl.
CPC ............ *C08G 63/916* (2013.01); *C07C 67/03* (2013.01); *C07C 67/08* (2013.01); *C07C 69/82* (2013.01); *C08G 18/36* (2013.01); *C08G 18/4213* (2013.01); *C08G 18/4288* (2013.01); *C08G 18/735* (2013.01); *C08G 18/755* (2013.01); *C08G 63/553* (2013.01); *C08J 11/24* (2013.01); *C09D 175/06* (2013.01); *C07C 2601/14* (2017.05); *C08G 2101/0025* (2013.01); *C08J 2367/02* (2013.01); *Y02W 30/706* (2015.05)

(58) Field of Classification Search
CPC ................ C08G 18/36; C08G 18/4213; C08G 18/4288; C08G 18/735; C08G 18/755; C08G 63/553; C08G 63/916; C08G 2101/0008; C08G 2101/0025; C08J 11/24; C08J 2367/02; C08L 67/08; C09D 167/07; C09D 175/06; Y02W 30/706
See application file for complete search history.

(56) References Cited

U.S. PATENT DOCUMENTS

| | | | |
|---|---|---|---|
| 2,793,220 A | 5/1957 | Barrett et al. | |
| 4,054,561 A | 10/1977 | Strauss et al. | |
| 4,079,028 A | 3/1978 | Emmons | |
| 4,096,102 A | 6/1978 | Strauss | |
| 4,155,892 A | 5/1979 | Emmons | |
| 4,223,068 A * | 9/1980 | Carlstrom | C08G 18/4213 428/304.4 |

(Continued)

FOREIGN PATENT DOCUMENTS

| | | |
|---|---|---|
| CA | 2215798 | 10/1996 |
| EP | 0558907 | 9/1993 |

(Continued)

OTHER PUBLICATIONS

D. Paszun et al., Ind. Eng. Chem. Res. 36 (1997) 1373.

(Continued)

*Primary Examiner* — John Cooney
(74) *Attorney, Agent, or Firm* — Dilworth IP LLC

(57) ABSTRACT

Polyester polyols made from thermoplastic polyesters are disclosed. The polyols can be made by heating a thermoplastic polyester such as virgin PET, recycled PET, or mixtures thereof, with a glycol to give a digested intermediate, which is then condensed with a dimer fatty acid to give the polyol. The invention includes a polyester polyol comprising recurring units of a glycol-digested thermoplastic polyester and a dimer fatty acid. The polyester polyol can also be made in a single step by reacting the thermoplastic polyester, glycol, and dimer acid under conditions effective to produce the polyol. High-recycle-content polyols having desirable properties and attributes for formulating polyurethane products, including aqueous polyurethane dispersions, can be made. The polyols provide a sustainable alternative to bio- or petrochemical-based polyols.

20 Claims, No Drawings

(56) References Cited

U.S. PATENT DOCUMENTS

| | | |
|---|---|---|
| 4,371,469 A | 2/1983 | Foglia |
| 4,423,179 A | 12/1983 | Guadliardo |
| 4,439,550 A | 3/1984 | Brennan |
| 4,546,169 A | 10/1985 | Chandler |
| 4,602,079 A | 7/1986 | Vinches |
| 4,608,432 A | 8/1986 | Magnus |
| 4,720,571 A | 1/1988 | Trowell |
| 4,758,607 A | 7/1988 | Hallmark et al. |
| 5,138,027 A | 8/1992 | Van Beek |
| 5,155,163 A | 10/1992 | Abeywardena |
| 5,252,615 A | 10/1993 | Rao et al. |
| 5,281,654 A | 1/1994 | Eisenhart |
| 5,502,247 A | 3/1996 | Bartos |
| 5,552,478 A | 9/1996 | Fisher |
| 5,574,127 A | 11/1996 | Sau |
| 5,608,000 A | 3/1997 | Duan |
| 5,756,554 A | 5/1998 | Fisher |
| 5,763,526 A | 6/1998 | Harakawa |
| 5,922,779 A | 7/1999 | Hickey |
| 5,932,666 A | 8/1999 | Fisher |
| 5,948,828 A | 9/1999 | Reck |
| 5,958,601 A | 9/1999 | Salsman |
| 6,281,373 B1 | 8/2001 | Sato |
| 6,337,366 B1 | 1/2002 | Amick |
| 6,339,125 B1 | 1/2002 | Bechara |
| 6,359,022 B1 | 3/2002 | Hickey |
| 6,573,304 B1 | 6/2003 | Durand |
| 6,630,601 B1 | 10/2003 | Inada |
| 6,635,723 B1 | 10/2003 | Maier |
| 6,642,350 B1 | 11/2003 | Asakawa |
| 6,664,363 B1 | 12/2003 | Faunce |
| 6,670,429 B2 | 12/2003 | Appelman |
| 6,887,909 B2 | 5/2005 | Kawamura et al. |
| 7,045,573 B2 | 5/2006 | Mayer |
| 7,192,988 B2 | 3/2007 | Smith |
| 7,342,068 B2 | 3/2008 | Klingenberg |
| 7,560,526 B2 | 7/2009 | Shieh |
| 8,334,357 B2 | 12/2012 | Schieferstein |
| 8,454,793 B2 | 6/2013 | Carter |
| 8,461,213 B2 | 6/2013 | Muenzenberg |
| 8,524,649 B2 | 9/2013 | Leyrer |
| 8,673,275 B2 | 3/2014 | Kim |
| 8,697,797 B2 | 4/2014 | Suau |
| 8,871,817 B2 | 10/2014 | Tuerk |
| 2007/0270518 A1 | 11/2007 | Nutzel |
| 2009/0131625 A1 | 5/2009 | Kurian |
| 2014/0134534 A1 | 5/2014 | Sacripante |

FOREIGN PATENT DOCUMENTS

| | | |
|---|---|---|
| EP | 2565226 | 3/2013 |
| JP | 2004-307583 | * 11/2004 |
| JP | 2004307583 | 4/2014 |
| WO | 0024802 | 5/2000 |
| WO | 200075252 | 12/2000 |
| WO | 2004083274 | 9/2004 |
| WO | 2008067967 | 8/2008 |
| WO | 2011134872 | 11/2011 |
| WO | 2012135625 | 10/2012 |
| WO | 2013041552 | 3/2013 |
| WO | 2013154874 | 10/2013 |

OTHER PUBLICATIONS

N. Ikladious, J. Elast. Plast. 32 (2000) 140.
K. Troev et al., J. Appl. Polym. Sci. 90 (2003) 1148.
I. Vitkauskiene, Chemija 19 (2008) 29.
J. Cheong, A-P Coatings J., Aug. 2009, 23.
M. van der Wouden, UTECH Asia '95, Paper # 34.
M. van der Wouden, UTECH '94, Paper # 21.
M. Mazurek et al. Polym. Adv. Technol. 25 (2014) 1273.

* cited by examiner

US 9,840,584 B2

POLYESTER POLYOLS FROM THERMOPLASTIC POLYESTERS AND DIMER FATTY ACIDS

FIELD OF THE INVENTION

The invention relates to polyol compositions produced from thermoplastic polyesters, including recycled or virgin polyethylene terephthalate. The polyols, which are useful for formulating polyurethanes and other condensation polymers, incorporate a dimer fatty acid.

BACKGROUND OF THE INVENTION

Aromatic polyester polyols are commonly used intermediates for the manufacture of polyurethane products, including flexible and rigid foams, polyisocyanurate foams, coatings, sealants, adhesives, and elastomers. The aromatic content of these polyols contributes to strength, stiffness, and thermal stability of the urethane product.

Commonly, the aromatic polyester polyol is made by condensing aromatic diacid, diesters, or anhydrides (e.g., terephthalic acid, dimethyl terephthalate) with glycols such as ethylene glycol, propylene glycol, diethylene glycol, or the like. These starting materials usually derive exclusively from petrochemical sources.

As companies increasingly seek to offer products with improved sustainability, the availability of intermediates produced from bio-renewable and/or recycled materials becomes more leveraging. However, there remains a need for these products to deliver equal or better performance than their traditional petroleum-based alternatives at a comparable price point.

Bio-renewable content alone can be misleading as an indicator of "green" chemistry. For example, when a food source such as corn is needed to provide the bio-renewable content, there are clear trade-offs between feeding people and providing them with performance-based chemical products. Additionally, the chemical or biochemical transformations needed to convert sugars or other bio-friendly feeds to useful chemical intermediates such as polyols can consume more natural resources and energy and can release more greenhouse gases and pollutants into the environment than their petro-based alternatives in the effort to achieve "green" status.

Waste thermoplastic polyesters, including waste polyethylene terephthalate (PET) streams (e.g., from plastic beverage containers), provide an abundant source of raw material for making new polymers. Usually, when PET is recycled, it is used to make new PET beverage bottles, PET fiber, or it is chemically transformed to produce polybutylene terephthalate (PBT). Other recycled raw materials are also available. For example, recycled propylene glycol is available from aircraft or RV deicing and other operations, and recycled ethylene glycol is available from spent vehicle coolants.

Urethane formulators demand polyols that meet required specifications for color, clarity, hydroxyl number, functionality, acid number, viscosity, and other properties. These specifications will vary and depend on the type of urethane application. For instance, rigid foams generally require polyols with higher hydroxyl number than the polyols used to make flexible foams.

Polyols suitable for use in making high-quality polyurethanes have proven difficult to manufacture from recycled materials, including recycled polyethylene terephthalate (rPET). Many references describe digestion of rPET with glycols (also called "glycolysis"), usually in the presence of a catalyst such as zinc or titanium. Digestion converts the polymer to a mixture of glycols and low-molecular-weight PET oligomers. Although such mixtures have desirably low viscosities, they often have high hydroxyl numbers or high levels of free glycols. Frequently, the target product is a purified bis(hydroxyalkyl) terephthalate (see, e.g., U.S. Pat. Nos. 6,630,601, 6,642,350, and 7,192,988) or terephthalic acid (see, e.g., U.S. Pat, No. 5,502,247). Some of the efforts to use glycolysis product mixtures for urethane manufacture are described in a review article by D. Paszun and T. Spychaj (*Ind. Eng. Chem. Res.* (1997) 1373.

Most frequently, ethylene glycol is used as the glycol reactant for glycolysis. This is sensible because it minimizes the possible reaction products. Usually, the glycolysis is performed under conditions effective to generate bis(hydroxyethyl) terephthalate ("BHET"), although sometimes the goal is to recover pure terephthalic acid. When ethylene glycol is used as a reactant, the glycolysis product is typically a crystalline or waxy solid at room temperature. Such materials are less than ideal for use as polyol intermediates because they must be processed at elevated temperatures. Polyols are desirably free-flowing liquids at or close to room temperature.

Dimer fatty acids (also called "dimerized fatty acids" or "dimer acids") are chemical intermediates made by dimerizing unsaturated fatty acids (e.g., oleic acid, linoleic acid, ricinoleic acid) in the presence of a catalyst, such as a bentonite or montmorillonite clay. Commercially available dimer fatty acids are usually mixtures of products in which the dimer acid predominates. Some commercial dimer acids are made by dimerizing tall oil fatty acids. Dimer fatty acids are commonly used to synthesize polyimide resins used in inks and hot-melt adhesives (see, e.g., U.S. Pat. No. 5,138, 027). They are also components of alkyd resins, adhesives, surfactants, and other products.

Less commonly, dimer fatty acids are used as urethane components, particularly when the urethane includes a recycled PET-based polyol. One exception is JP 2004-307583, which describes a method for producing a polyester polyol and cured polyurethane. The '583 publication describes a two-step method in which recycled PET is digested with a glycol in the presence of a transesterification catalyst. The resulting product is then reacted with a polybasic acid having 20 or more carbons and no polymerizable double bond. Dimer acids are taught as suitable polybasic acids for the second step. The reaction product is subsequently reacted with MDI to make a simple urethane coating. In the working examples, a relatively large proportion of dimer fatty acid is used (one or more equivalents of dimer acid per equivalent of recycled PET), and it is unclear whether satisfactory results could be obtained with less dimer fatty acid. The large proportion of dimer fatty acid also severely limits the amount of recycle content (rPET plus any recycled glycol) in the polyol.

Improved polyols are needed. In particular, the urethane industry needs sustainable polyols based in substantial part on recycled polymers such as the practically unlimited supply of recycled polyethylene terephthalate. Polyols with high recycle content that satisfy the demanding color, clarity, viscosity, functionality, and hydroxyl content requirements of polyurethane formulators would be valuable.

SUMMARY OF THE INVENTION

The invention relates to polyester polyols and processes for making them. In one aspect, the polyol is made by a process which comprises two steps. First, a thermoplastic polyester such as PET, recycled PET, or their mixtures, is heated with a glycol to give a digested intermediate. The intermediate is then condensed with a dimer fatty acid to give the polyol. In another aspect, the invention relates to a polyester polyol comprising recurring units of a glycol-digested thermoplastic polyester and a dimer fatty acid. In both aspects, the molar ratio of dimer fatty acid to thermoplastic polyester is less than 0.8, the molar ratio of glycol to thermoplastic polyester is at least 2.0, and the polyol has a hydroxyl number within the range of 25 to 800 mg KOH/g. The polyester polyol can also be made in a single step by reacting the thermoplastic polyester, glycol, and dimer acid under conditions effective to produce the polyol. Aqueous polyurethane dispersions made from the polyols are also included.

We surprisingly found that high-recycle-content polyols having desirable hydroxyl numbers, viscosities, appearance, and other attributes for formulating polyurethane products can be made by reacting, at certain equivalent ratios, a glycol-digested thermoplastic polyester, preferably a digested PET, and a dimer fatty acid. The polyols, which are valuable for formulating a variety of polyurethanes and related products—including polyurethane dispersions, flexible and rigid foams, coatings, adhesives, sealants, and elastomers—provide a sustainable alternative to bio- or petrochemical-based polyols.

DETAILED DESCRIPTION OF THE INVENTION

In one aspect, polyester polyols made by a two-step process are disclosed. A thermoplastic polyester is first heated with a glycol to give a digested intermediate. The digested intermediate is subsequently condensed with a dimer fatty acid to give the polyol.

Thermoplastic polyesters suitable for use are well known in the art. They are condensation polymers produced from the reaction of glycols and aromatic dicarboxylic acids or acid derivatives. Examples include polyethylene terephthalate (PET); polybutylene terephthalate (PBT); polytrimethylene terephthalate (PIT); glycol-modified polyethylene terephthalate (PETG); copolymers of terephthalic acid and 1,4-cyclohexanedimethanol (PCT); PCTA (an isophthalic acid-modified PCT); polyhydroxy alkanoates, e.g., polyhydroxybutyrate; copolymers of diols with 2,5-furandicarboxylic acid or dialkyl 2,5-furandicarboxylates, e.g., polyethylene furanoate; copolymers of 2,2,4,4-tetramethyl-1,3-cyclobutanediol with isophthalic acid, terephthalic acid or orthophthalic derivatives; dihydroferulic acid polymers; and the like, and mixtures thereof. Further examples of polyester thermoplastics are described in *Modern Polyesters: Chemistry and Technology of Polyesters and Copolyesters*, J. Scheirs and T. Long, eds., Wiley Series in Polymer Science, 2003, John Wiley & Sons, Ltd. Hoboken, N.J. Other examples of thermoplastic polyesters may be found in Chapters 18-20 of *Handbook of Thermoplastics*, O. Olabisi, ed., 1997, Marcel Dekker, Inc. New York. Suitable thermoplastic polyesters include virgin polyesters, recycled polyesters, or mixtures thereof. Polyethylene terephthalate is particularly preferred, especially recycled polyethylene terephthalate (rPET), virgin PET, and mixtures thereof. For more examples of suitable thermoplastic polyesters, see U.S. Pat. Appl. Publ. No. 2009/0131625, the teachings of which are incorporated herein by reference.

Recycled polyethylene terephthalate suitable for use in making the inventive polyester polyols can come from a variety of sources. The most common source is the post-consumer waste stream of PET from plastic bottles or other containers. The rPET can be colorless or contain dyes (e.g., green, blue, or other colors) or be mixtures of these. A minor proportion of organic or inorganic foreign matter (e.g., paper, other plastics, glass, metal, etc.) can be present. A desirable source of rPET is "flake" rPET, from which many of the common impurities present in scrap PET bottles have been removed in advance. Another desirable source of rPET is pelletized rPET, which is made by melting and extruding rPET through metal filtration mesh to further remove particulate impurities. Because PET plastic bottles are currently manufactured in much greater quantity than any recycling efforts can match, scrap PET will continue to be available in abundance.

Glycols suitable for use are well known. By "glycol," we mean a linear or branched, aliphatic or cycloaliphatic compound or mixture of compounds having two or more hydroxyl groups. Other functionalities, particularly ether or ester groups, may be present in the glycol. In preferred glycols, two of the hydroxyl groups are separated by from 2 to 10 carbons, preferably 2 to 5 carbons. Suitable glycols include, for example, ethylene glycol, propylene glycol, 1,3-propanediol, 1,2-butylene glycol, 1,3-butylene glycol, 1,4-butanediol, 2-methyl-1,3-propanediol, pentaerythritol, sorbitol, neopentyl glycol, glycerol, trimethylolpropane, 2,2, 4,4-tetramethyl-1,3-cyclobutanediol, 3-methyl-1,5-pentanediol, 1,4-cyclohexanedimethanol, 1,3-cyclohexanedimethanol, bisphenol A ethoxylates, diethylene glycol, dipropylene glycol, triethylene glycol, 1,6-hexanediol, tripropylene glycol, tetraethylene glycol, polyethylene glycols having a number average molecular weight up to about 400 g/mol, block or random copolymers of ethylene oxide and propylene oxide, and the like, and mixtures thereof. Propylene glycol is particularly preferred. In a preferred aspect, the glycol is a recycled glycol, especially recycled propylene glycol. Propylene glycol recovered from used deicing fluids is one example.

The thermoplastic polyester and glycol are heated, optionally in the presence of a catalyst, to give a digested intermediate. The digested intermediate will commonly be a mixture of glycol reactant, glycol(s) generated from the thermoplastic polyester, terephthalate oligomers, and other glycolysis products. For example, when PET or rPET is the thermoplastic polyester, the digested intermediate will include a mixture of glycol reactant, ethylene glycol (generated from the PET or rPET), bis(2-hydroxyalkyl) terephthalate ("BHAT"), higher PET oligomers, and other glycolysis products. Similar digested mixtures in various forms have been made and characterized previously (see, e.g., a Paszun et al., *Ind. Eng. Chem. Res.* 36 (1997) 1373 and N. Ikladious, *J. Elast. Plast.* 32 (2000) 140). Heating is advantageously performed at temperatures within the range of 80° C. to 260° C., preferably 100° C. to 240° C., more preferably 130° C. to 210° C., and most preferably 160° C. to 185° C.

In one aspect, when the thermoplastic polyester is polyethylene terephthalate, the digested intermediate comprises glycols and a terephthalate component. The terephthalate component preferably comprises, by gel permeation chromatography using ultraviolet detection, 45 to 70 wt. % of bis(hydroxyalkyl)terephthalates. In a preferred aspect, the terephthalate component further comprises 20 to 40 wt. % of terephthalate dimers. In another preferred aspect, the terephthalate component of the digested intermediate comprises 45 to 65 wt. % of bis(hydroxyalkyl)terephthalates, 20 to 35 wt. % of terephthalate dimers, and 5 to 15 wt. % of terephthalate trimers. In another preferred aspect, the terephthalate component comprises 50 to 60 wt. % of bis(hydroxyalkyl)-terephthalates, 25 to 30 wt. % of terephthalate dimers, and 8 to 12 wt. % of terephthalate trimers.

Catalysts suitable for making the digested intermediate are well known (see, e.g., K. Troev et al., *J. Appl. Polym. Sci.* 90 (2003) 1148). In particular, suitable catalysts comprise titanium, zinc, antimony, germanium, zirconium, manganese, or other metals. Specific examples include titanium alkoxides (e.g., tetrabutyl titanate), titanium(IV) phosphate, zirconium alkoxides, zinc acetate, lead acetate, cobalt acetate, manganese(II) acetate, antimony trioxide, germanium oxide, or the like, and mixtures thereof. Catalysts that do not significantly promote isocyanate reaction chemistries are preferred. The amount of catalyst used is typically in the range of 0.005 to 5 wt. %, preferably 0.01 to 1 wt. %, more preferably 0.02 to 0.7 wt. %, based on the total amount of polyol being prepared.

Usually, the digestion reaction is performed by heating the thermoplastic polyester, glycol(s), and any catalyst at least until the mixture liquefies and particles of the thermoplastic polyester are no longer apparent. Reaction times range from about 30 minutes to about 16 hours, more typically 1 to 10 hours, even more typically 3 to 8 hours, and will depend on the reaction temperature, source of the thermoplastic polyester, the particular glycol reactant used, mixing rate, desired degree of depolymerization, and other factors that are within the skilled person's discretion.

The molar ratio of glycol to thermoplastic polyester is at least 2.0, preferably 2.0 to 6.0, more preferably 2.5 to 4.5. When the glycol/thermoplastic polyester molar ratio is below 2.0, the products are often solids or too viscous to be practical for use as polyols. On the other hand, when the glycol/thermoplastic polyester molar ratio is greater than about 6, the hydroxyl numbers tend to exceed the practical upper limit of about 800 mg KOH/g.

In a second reaction step, the digested intermediate described above is condensed with a dimer fatty acid to give the inventive polyester polyol. As used herein, "dimer fatty acid" is synonymous with "dimerized fatty acid" or "dimer acid." Dimer fatty acids are chemical intermediates made by dimerizing unsaturated fatty acids (e.g., oleic acid, linoleic acid, linolenic acid, ricinoleic acid) in the presence of a catalyst, such as a bentonite or montmorillonite clay. Commercially available dimer fatty acids are usually mixtures of products in which the dimerized product predominates. Some commercial dimer acids are made by dimerizing tall oil fatty acids. Dimer fatty acids frequently have 36 carbons and two carboxylic acid groups. They may be saturated or unsaturated. They may also be hydrogenated to remove unsaturation. In a preferred aspect, the dimer fatty acid comprises dimerized oleic acid, trimerized oleic acid, dimerized linoleic acid, trimerized linolelic acid, dimerized linolenic acid, trimerized linolenic acid, or mixtures thereof. Suitable dimer fatty acids include Pripol™ dimer fatty acids (products of Croda) such as Pripol™ 1006, 1009, 1010, 1012, 1013, 1017, 1022, 1025, 1027, 1029, 1036, and 1098; Unidyme™ dimer acids (products of Arizona Chemical) such as Unidyme 10, 14, 18, 22, 35, M15, and M35; dimer acids available from Emery Oleochemicals, and FloraDyme™ dimer acids from Fiorachem Corporation.

Methods for synthesizing dimer fatty acids suitable for use are also known. Fatty acids having at least one carbon-carbon double bond are dimerized in the presence of a catalyst such as a montmorillonite, kaolinite, hectorite, or attapulgite clay (see, e.g., U.S. Pat. Nos. 2,793,220, 4,371, 469, 5,138,027, and 6,281,373, the teachings of which are incorporated herein by reference; see also WO 2000/075252 and CA 104511).

The reaction between the digested intermediate and the dimer fatty acid is performed under conditions effective to promote condensation between one or more acid groups of the dimer fatty acid and hydroxyl groups present in the digested intermediate. The condensation is preferably performed by heating at temperatures within the range of 80° C. to 260° C., preferably 100° C. to 240° C., more preferably 130° C. to 230° C., and most preferably 160° C. to 210° C. Water generated in this reaction is advantageously removed from the reaction mixture as it forms. On a lab scale, it is convenient to use a Dean-Stark trap or similar apparatus to remove the water of reaction, but other means will be more practical on a larger scale. Continuous processes for water removal, such as vacuum stripping, wiped-film evaporation, and the like, may be desirable. The condensation reaction is normally continued until a pre-determined amount of water has been collected or a target acid number and/or hydroxyl number is reached for the product.

The molar ratio of dimer fatty acid to thermoplastic polyester is less than 0.8, preferably less than 0.7, more preferably less than 0.6. The molar ratio of dimer fatty acid to thermoplastic polyester is preferably within the range of 0.1 to 0.6, more preferably 0.2 to 0.5. When the molar ratio is less than 0.1, there is too little benefit from including the dimer fatty acid in terms of generating useful polyols (for instance, the hydroxyl numbers reach or exceed their useful upper limit). When the molar ratio is greater than 0.8, formulation cost is higher than desirable, recycle content drops, and there is little or no additional performance benefit.

As long as some dimer fatty acid is used to make the polyol, one or more other dicarboxylic acids can also be included. Instead of including a dicarboxylic acid, a diester, or an anhydride can be used. Suitable dicarboxylic acids include, for example, glutaric acid, adipic acid, succinic acid, cyclohexane dicarboxylic acids, maleic acid, fumaric acid, itaconic acid, phthalic acid, 1,5-furandicarboxylic acid, isophthalic acid, and anhydrides thereof (e.g., maleic anhydride, phthalic anhydride, itaconic anhydride, and the like). Mixtures of dicarboxylic acids can be used, including, e.g., the commercially available mixture of dibasic acids known as "DBA." A typical DBA composition might contain 51-61 wt. % glutaric acid, 18-28 wt. % succinic acid, and 15-26 wt. % adipic acid.

Preferably, when another dicarboxylic acid is included, the dimer fatty acid is present in a greater molar proportion compared with the additional dicarboxylic acid. When the molar amount of dicarboxylic acid exceeds that of the dimer fatty acid, the polyol product has a greater tendency to solidify, has higher viscosity, and is prone to settling.

In another aspect, the polyester polyol is made in a single step by reacting the thermoplastic polyester, glycol, and dimer fatty acid under conditions effective to produce the polyol. As with polyols made using the two-step process, the molar ratio of dimer fatty acid to thermoplastic polyester is less than 0.8, the molar ratio of glycol to thermoplastic polyester is at least 2.0, and the resulting polyol has a hydroxyl number within the range of 25 to 800 mg KOH/g. When the single-step process is used, it is preferred to utilize a condensation system that returns glycols to the reaction vessel while allowing removal of water, as removal of too much glycol can result in cloudy or opaque polyols. Example 11 below illustrates the single-step process.

The inventive polyester polyols have hydroxyl numbers within the range of 25 to 800 mg KOH/g, preferably 40 to 500 mg KOH/g, more preferably 200 to 400 mg KOH/g. Hydroxyl number can be measured by any accepted method for such a determination, including, e.g., ASTM E-222 ("Standard Test Methods for Hydroxyl Groups Using Acetic Anhydride Acetylation").

The inventive polyols preferably have average hydroxyl functionalities (i.e., the average number of —OH groups per molecule) within the range of 1.5 to 3.5, more preferably 1.8 to 2.5, and most preferably 2.0 to 2.4.

The inventive polyols are flowable liquids under ambient conditions. Preferably, the polyols have viscosities measured at 25° C. less than 30,000 cP, more preferably less than 20,000 cP, most preferably less than 10,000 cP. A preferred range for the polyol viscosity is 300 to 5,000 cP, more preferably 500 to 3,900 cP. Viscosity can be determined by any industry-accepted method. It is convenient to use, for instance, a Brookfield viscometer (such as a Brookfield DV-III Ultra rheometer) fitted with an appropriate spindle, and to measure a sample at several different torque settings to ensure an adequate confidence level in the measurements.

The polyols preferably have low acid numbers. Urethane manufacturers will often require that a polyol have an acid number below a particular specification. Low acid numbers can be ensured by driving the condensation step (with dimer fatty acid) to the desired level of completion or by adding a neutralizing agent (e.g., sodium hydroxide) at the conclusion of the condensation step. Preferably, the polyols have an acid number less than 30 mg KOH/g, more preferably less than 10 mg KOH/g, and most preferably less than 5 mg KOH/g. As suggested above, it is acceptable practice to adjust acid numbers if necessary for a particular application with an acid scavenger such as, for example, an epoxide derivative, and this treatment can be performed by the manufacturer, distributor, or end user.

An advantage of the polyester polyols is their reduced reliance on bio- or petrochemical sources for raw material. Preferably, the polyols include greater than 10 wt. %, more preferably greater than 25 wt. %, most preferably greater than 50 wt. % of recycle content. A preferred range for the recycle content is 25 to 98,5 wt. %. By "recycle content," we mean the combined amounts of thermoplastic polyester and any recycled glycol or dicarboxylic acid. Some glycols, such as propylene glycol or ethylene glycol, are available as recovered or recycled materials. For instance, propylene glycol is used in deicing fluids, and after use, it can be recovered, purified, and reused. Usually, the dimer fatty acid is prepared from renewable resources. Recycle content can be calculated, for instance, by combining the masses of thermoplastic polyester and any recycled PG or recycled dicarboxylic acids, dividing this sum by the total mass of reactants (glycols, thermoplastic polyester, dimer acid, and any dicarboxylic acids), and then multiplying the result by 100.

Although performance in the ultimate end use is paramount, urethane manufacturers like to purchase polyols that look good. When other considerations are equal, a transparent (or nearly transparent) polyol may be more attractive than an opaque one. ("Dispersion polyols" or "polymer polyols," which are common components of the load-bearing, high-resiliency urethane foams used in automotive seating or furniture applications, are a notable exception; they are supposed to appear opaque.) Unlike known polyols that are made by reacting thermoplastic polyester digestion products with dicarboxylic acids such as succinic acid or phthalic anhydride, which are often opaque, the inventive polyols are frequently transparent or nearly so. This is particularly true when the molar ratio of glycol to thermoplastic polyester is kept within the range of 2.5 to 4.

Yet another desirable polyol attribute is the absence of settling, particularly upon prolonged storage. When settling is substantial, the polyol might have to be filtered or otherwise treated to remove the solids content; this is preferably avoided. Preferred inventive polyols exhibit no settling or only a slight degree of settling, and more preferred polyols exhibit no evidence of settling.

In another aspect, the invention includes a polyester polyol comprising recurring units of a glycol-digested thermoplastic polyester and a dimer fatty acid, wherein the molar ratio of dimer fatty acid to thermoplastic polyester is less than 0.8, the molar ratio of glycol to thermoplastic polyester is at least 2.0, and the polyol has a hydroxyl number within the range of 25 to 800 mg KOH/g. The glycol-digested thermoplastic polyester and dimer fatty acid have already been described above. "Recurring units" means that the polyester polyol includes one or more units derived from each of the dimer fatty acid and the glycol-digested thermoplastic polyester.

In a specific aspect, the invention relates to a process which comprises: (a) heating virgin PET, recycled PET, or a mixture thereof with propylene glycol in the presence of a zinc or titanium catalyst to give a digested intermediate; and (b) condensing the intermediate with a dimer fatty acid to give the polyol; wherein the molar ratio of dimer fatty acid to PET is less than 0.6, the molar ratio of glycol to PET is within the range of 2.5 to 4.5, and the polyol has a hydroxyl number within the range of 40 to 500 mg KOH/g, a viscosity at 25° C. less than 5,000 cP, and a recycle content as defined herein greater than 25 wt. %.

The inventive polyester polyols can be used to formulate a wide variety of polyurethane products. By adjusting the proportion of dimer fatty acid used, a desired degree of polyol hydrophobicity can be "dialed in." The ability to control hydrophobicity is particularly valuable in the coatings industry. The polyols can be used for cellular, microcellular, and non-cellular applications including flexible foams, rigid foams (including polyisocyanurate foams), urethane dispersions, coatings, adhesives, sealants, and elastomers. The resulting polyurethanes are potentially useful for automotive and transportation applications, building and construction products, marine products, packaging foam, flexible slabstock foam, carpet backing, appliance insulation, cast elastomers and moldings, footwear, biomedical devices, and other applications.

Further, the inventive polyester polyols may be derivatized to form mono-, di- and polyacrylates via esterification or transesterification with acrylic acid or methacrylic acid-derived raw materials. Examples of (meth)acrylation raw materials suitable for forming (meth)acrylate derivatives of the inventive polyester polyols include acryloyl chloride, methacryloyl chloride, methacrylic acid, acrylic acid, methyl acrylate, methyl methacrylate, and the like, or mixtures thereof. Such (meth)acrylate-derivatized inventive polyester polyols are useful for radiation or UV cure coating formulations or applications. Prepolymers of the inventive polyester polyols may be derivatized to form urethane (meth)acrylates via reaction with hydroxyethyl (meth)acrylate. The resulting urethane acrylates may also be used in radiation or UV-cure coating formulations or applications.

In a particular aspect, the invention relates to aqueous polyurethane dispersions made from the inventive polyester polyols. We found that the dimer fatty acid-modified polyols are readily formulated into aqueous polyurethane dispersions having a desirable balance of properties, including high solids, low viscosities, and a low tendency to settle. Numerous ways to formulate aqueous polyurethane dispersions are known and suitable for use. Preferably, the polyurethane dispersion is made by emulsifying an isocyanate-terminated prepolymer in water with the aid of an emulsifying agent. Water, a water-soluble polyamine chain extender, or a combination thereof may be used to react with the emulsified prepolymer. The prepolymer is preferably made by reacting an inventive polyester polyol, a hydroxy-functional emulsifier, one or more auxiliary polyols, and one or more polyisocyanates. The aqueous polyurethane dispersions are preferably used to formulate water-borne coatings, adhesives, sealants, elastomers, and similar urethane products, and they are particularly valuable for reducing reliance on solvents. For instance, the dispersions can be used to formulate low- or zero-VOC compositions.

Polyisocyanates suitable for use in making the prepolymers are well known; they include aromatic, aliphatic, and cycloaliphatic polyisocyanates. Examples include toluene diisocyanates (TDs), MDIs, polymeric MDIs, naphthalene diisocyanates (NDIs), hydrogenated MDIs, trimethyl- or tetramethylhexamethylene diisocyanates (TMDIs), hexamethylene diisocyanate (HDI), isophorone diisocyanates (IPDIs), cyclohexane diisocyanates (CHDIs), xylylene diisocyanates (XDI), hydrogenated XDIs, and the like. Aliphatic diisocyanates, such as hexamethylene diisocyanate and isophorone diisocyanates are particularly preferred.

Auxiliary polyols suitable for use are also well known. They include polyether polyols, aliphatic polyester polyols, aromatic polyester polyols, polycarbonate polyols, glycols, and the like. Preferred auxiliary polyols have average hydroxyl functionalities within the range of 2 to 6, preferably 2 to 3, and number average molecular weights within the range of 500 to 10,000, preferably 1,000 to 8,000. Preferred polyester polyols are condensation products of dicarboxylic acids and diols or triols (e.g., ethylene glycol, propylene glycol, 2-methyl-1,3-propanediol, 3-methyl-1,5-pentanediol, 1,4-butanediol, neopentyl glycol, glycerin, trimethylolpropane, 1,4-cyclohexanedimethanol, bisphenol A ethoxylates), especially diols. The dicarboxylic acids can be aliphatic (e.g., glutaric, adipic, succinic) or aromatic (e.g., phthalic), preferably aliphatic.

A hydroxy-functional emulsifier is also used to make the polyurethane dispersions. The role of this component is to impart water-dispersibility to the prepolymer, usually upon its combination with water and a neutralizing agent, such as an acid or base reactant. Thus, in one aspect, the hydroxy-functional emulsifier is an acid-functional diol such as dimethylolpropionic acid (DMPA) or dimethylolbutanoic acid (DMBA). The acid functionality in the resulting prepolymer allows for neutralization with an amine or other basic reactant to generate a water-dispersible urethane. The hydroxy-functional emulsifier can also be an amine, such as N-methyldiethanolamine. Neutralization of the resulting prepolymer with an acidic reagent renders it water dispersible. In other aspects, the hydroxy-functional emulsifier is nonionic, e.g., a polyethylene glycol monomethyl ether. In another aspect, the hydroxy-functional emulsifier may be a monol- or diol-functionalized poly(ethylene oxide), such as for example Ymer™ N120 dispersing monomer (product of Perstorp), or the methyl ether of polyethylene glycol. Additionally, non-reactive, so-called "external emulsifiers," such as the triethanolamine salt of dodecylbenzene sulfonic acid, may be included in the aqueous phase to assist in the emulsification and stabilization of the prepolymer and resulting polyurethane dispersion.

In certain aspects, a chain terminator may be used to control the molecular weight of polyurethane polymer contained within the aqueous polyurethane dispersion. Monofunctional compounds, such as those containing hydroxyl, amino, and thio groups that have a single active hydrogen-containing group, are suitable chain terminators. Examples include alcohols, amines, thiols, and the like, especially primary and secondary aliphatic amines.

Chain extenders can also be included in making the polyurethane dispersion. In some aspects, the chain extender is added in an amount sufficient to react 5 to 105 mole % of free NCO groups present. Suitable chain extenders contain at least two functional groups that are capable of reacting with isocyanates, e.g., hydroxyl, thio, or amino groups in any combination. Suitable chain extenders include, for example, diols (ethylene glycol, propylene glycol, diethylene glycol, neopentyl glycol, 1,4-butanediol, 2-methyl-1,3-propanediol, 3-methyl-1,5-pentanediol, 1,4-cyclohexanedimethanol, and the like), di- and polyamines (ethylenediamine, diethylenetriamine, Jeffamine® T-403, Jeffamine® D-230, Jeffamine® ED 2001, Jeffamine® ED-600, Jeffamine® ED 900, 1,6-hexamethylenediamine, butylenediamine, hydrazine, piperazine, N-hydroxyethyl ethylenediamine) alkanolamines (ethanolamine, diethanolamine, N-methyl diethanolamine, and the like), dithiols, and the like. Diol chain extenders are preferably added during the preparation of the prepolymer, and prior to emulsification in water.

In a specific example, shown below, the dimer fatty acid-modified polyester polyol, an acid-functional diol (DMPA), and auxiliary polyols (polyethylene glycol 200 and a polyester polyol made from 3-methyl-1,5-pentanediol and adipic acid) are combined and reacted with a mixture of aliphatic diisocyanates (hexamethylene diisocyanate and isophorone diisocyanate) in the presence of a tin catalyst (dibutyltin dilaurate) or a bismuth catalyst (such as bismuth dioctanoate) and a solvent (acetone). The resulting prepolymer is then dispersed in a mixture of water, triethanolamine (neutralizing agent), and a silicone defoamer. The resulting product is an aqueous polyurethane dispersion having high solids content (30%), low viscosity, and desirable settling properties.

For more examples of suitable approaches for preparing aqueous polyurethane dispersions, see U.S. Pat. Nos. 5,155,163; 5,608,000; 5,763,526; 6,339,125; 6,635,723; 7,045,573; and 7,342,068, the teachings of which are incorporated herein by reference.

In another aspect, the invention relates to associative rheology modifiers made from the dimer fatty acid-modified polyester polyols. By "associative rheology modifier," we mean an additive used to thicken or after the viscosity of a product. Associative thickening may involve dynamic, non-specific interactions of hydrophobic end groups of a thickener molecule with itself and with other components of a formulation. Associative thickening is particularly applicable to water-based paints and coatings, where the rheology modifier, by virtue of inter- and intra-molecular network formations, is able to modify gloss, flow, shear, leveling, spatter resistance, or other properties. In addition to paints or coatings, suitable formulations might include sealants, pharmaceuticals, cosmetics, or other products that can benefit from rheology modification. Certain categories of associative rheology modifiers are well known and can be formulated using the inventive polyester polyols alone or, more often, in combination with other polyol components. Such rheology modifiers include, for example, hydrophobically modified ethoxylated urethanes ("HEUR"), hydrophobically modified alkali-swellable emulsions ("HASE"), and hydrophobically modified polyethers ("HMPE"). Suitable HASE modifiers include, e.g., hydrophobically modified polyacrylates. A typical HEUR might be assembled from a hydrophilic diol (e.g., a polyethylene glycol of 6,000-8,000 g/mol), a polyisocyanate, and a hydrophobic mono or diol. The inventive polyester polyols can be utilized to supplement or replace the hydrophobic mono or diol. For examples of HEUR, HASE, and HMPE associative rheology modifiers and their methods of preparation, see U.S. Pat. Nos. 8,871, 817; 8,673,275; 8,697,797; 8,524,649; 8,461,213; 8,334, 357; 6,337,366; 5,574,127; 5,281,654; 4,155,892; and 4,079,028 the teachings of which are incorporated herein by reference.

The following examples merely illustrate the invention; the skilled person will recognize many variations that are within the spirit of the invention and scope of the claims.

Preparation of Dimer Fatty Acid-Modified Polyols: General Procedure

A reactor equipped with an overhead mixer, condenser, heating mantle, thermocouple, and nitrogen inlet is charged with zinc acetate dihydrate (0.55 wt. %), titanium(V) butoxide (500-1000 ppm), or no catalyst (Ex. 32); recycled polyethylene terephthalate pellets; and glycol in the proportions shown in Table 1. The mixture is heated without stirring to about 130° C. Stirring is then commenced at 60 rpm, and heating continues until the reactor contents reach 180° C. The mixture is heated until no particles of recycled PET remain (about 4 h). When the digestion reaction is considered complete, the mixture is cooled to about 100° C. Dimer fatty acid (and/or dicarboxylic acid) is added (see Table 1 for mole ratios), and the mixing rate is increased (200 rpm). The dimer fatty acid used is Pripol™ 1017, product of Croda. When the addition is complete, a Dean-Stark trap is introduced between the reactor and condenser, and heating to 200° C. is resumed. Water generated in the condensation reaction is removed until roughly the theoretical amount is removed. When the reaction is complete, the polyol product is allowed to cool to 100° C. and is then decanted from the reactor and filtered through cheesecloth.

The glycols used are propylene glycol, 2-methyl-1,3-propanediol, 3-methyl-1,5-pentanediol, diethylene glycol, and 1,4-cyclohexanedimethanol. In most examples, the dimer fatty acid (and/or dicarboxylic acid) is added following digestion of the recycled PET with the glycol, as described above. In a few examples, however, the dimer fatty acid (and/or dicarboxylic acid) is added at the outset, i.e., before digestion. Control runs in which no dimer fatty acid or dicarboxylic acid is used are also included. In some examples, the dicarboxylic acid is "DBA," a well-known dibasic acid mixture available from INVISTA and other suppliers that contains primarily glutaric acid, succinic acid, and adipic acid. A typical DBA composition might contain 51-61 wt. % glutaric acid, 18-28 wt. % succinic acid, and 15-25 wt. % adipic acid. The dicarboxylic acids (or anhydrides) used are succinic acid, phthalic anhydride, adipic acid, and DBA. The digestions are catalyzed by zinc acetate unless otherwise indicated in the tables.

"Recycle content" as used herein (wt. %) is determined by combining the masses of recycled glycol and recycled thermoplastic polyester, dividing this sum by the total mass of reactants (e.g., glycols, rPET, dimer acid, and any dicarboxylic acids), and then multiplying the result by 100.

Hydroxyl numbers and acid numbers are determined by standard methods (ASTM E-222 and ASTM D3339, respectively).

Viscosities are measured at 25° C. using a Brookfield DV-III Ultra rheometer with spindle #31 at 25%, 50%, and 75% torque.

Color, clarity, and degree of settling are evaluated visually.

Results:

As shown in Tables 1 and 2, polyols having hydroxyl numbers below 800 mg KOH/g (especially below 600 mg KOH/g), favorable viscosities (especially 1000 to 4000 cP), and recycle contents greater than 10 wt. % (especially greater than 25%) can be made by reacting glycol-digested recycled PET with dimer fatty acids, where the molar ratio of glycol to rPET is at least 2.0 and the molar ratio of dimer fatty acid to rPET is less than 0.8. Condensing the glycol-digested rPET with a dimer fatty acid also makes it possible to generate polyols that are in many cases transparent, especially when the glycol to rPET molar ratio is within the range of 2.5 to 4.5. If desired, some dicarboxylic acid (e.g., succinic acid) can be included along with the dimer fatty acid, but such products are typically opaque. Settling is generally avoided by using the preferred glycol to rPET molar ratio range of 2.5 to 4.5.

Comparative examples are provided in Tables 3 and 4. In some comparative examples, the glycol/rPET ratio is below 2.0, which typically results in an opaque and highly viscous or solid product. In other comparative examples, the glycol/rPET ratio is 2.0 or greater, but the dimer fatty acid is omitted in favor of a dicarboxylic acid or anhydride (e.g., succinic acid, phthalic anhydride, or DBA). The products are opaque and tend to be viscous. When the glycol/rPET ratio is high (6.0 or 9.0), the hydroxyl number of the product is greater than 800 mg KOH/g. Other comparative examples show that digestion of the rPET alone gives a product with desirably low viscosity but the hydroxyl numbers are too high to be useful.

Aqueous Polyurethane Dispersion

A DFA-modified polyol prepared as in Example 30 is used to formulate a polyurethane dispersion as follows:

A prepolymer is generated by combining the DFA-modified polyol (53.4 g), P2010 polyol (3-methyl-1,5-pentanediol adipate, 2000 mol. wt., 17.1 g, product of Kuraray), dimethylpropionic acid (9.5 g), polyethylene glycol (PEG 200, 1.33 g), acetone (140 g), and dibutyltin dilaurate (0.24 g) with hexamethylene diisocyanate (8.8 g) and isophorone diisocyanate (64.8 g). The mixture is mixed well and allowed to react at 60° C. for 7.5 h to form the prepolymer mixture.

The prepolymer mixture (261 g) is combined and rapidly mixed with water (456 g), triethanolamine (14.4 g), and Byk® 028 silicone defoamer (6.21 g of 10% solution in water) to generate an aqueous polyurethane dispersion. The resulting light-green dispersion has 29.7% solids, pH=8.05, and viscosity=809 cP at 21.5° C.

TABLE 1

Dimer Fatty Acid-Modified Polyol Preparation: Inventive Examples

| Ex | glycol(s) | description | glycol/rPET (mol/mol) | DFA/rPET (mol/mol) | DA/rPET (mol/mol) |
|---|---|---|---|---|---|
| 1 | 2-methyl-1,3-propanediol | Add dimer fatty acid (DFA) after digestion | 3.0 | 0.50 | — |
| 2 | 2-methyl-1,3-propanediol | Add DFA after digestion | 3.0 | 0.50 | — |
| 3 | propylene glycol (PG) | Add DFA after digestion | 6.0 | 0.50 | — |
| 4 | propylene glycol | Add DFA after digestion | 6.0 | 0.50 | — |
| 5 | propylene glycol | Add DFA after digestion | 9.0 | 0.50 | — |
| 6 | propylene glycol | Add DFA after digestion | 4.0 | 0.50 | — |
| 7 | propylene glycol | Add DFA after digestion | 6.0 | 0.50 | — |
| 8 | propylene glycol | Add DFA after digestion | 3.0 | 0.50 | — |
| 9 | propylene glycol | Add DFA after digestion | 3.0 | 0.25 | — |
| 10 | propylene glycol | Add DFA after digestion | 3.0 | 0.125 | — |
| 11 | propylene glycol | DFA is added at the outset | 3.0 | 0.25 | — |
| 12 | propylene glycol | Add DFA after digestion | 3.0 | 0.25 | — |
| 13 | propylene glycol | Add DFA and succinic acid after digestion | 3.0 | 0.25 | 0.25 |
| 14 | propylene glycol | Add DFA after digestion | 2.0 | 0.25 | — |
| 15 | propylene glycol | Add DFA and succinic acid after digestion | 3.0 | 0.375 | 0.125 |
| 16 | propylene glycol | Add DFA after digestion | 2.0 | 0.20 | — |
| 17 | propylene glycol | Add DFA after digestion | 3.0 | 0.40 | — |
| 18 | propylene glycol | Green pellets used. Add DFA after digestion | 3.0 | 0.50 | — |
| 19 | PG + 1,4-cyclohexanedimethanol | Add DFA after digestion | 3.0 | 0.50 | — |
| 20 | propylene glycol | Green pellets used. Add DFA after digestion | 3.0 | 0.50 | — |
| 21 | propylene glycol | Dilinoleic acid used as the DFA, and added after digestion | 3.0 | 0.50 | — |
| 22 | propylene glycol | Add DFA after digestion | 3.0 | 0.50 | — |
| 23 | propylene glycol | Add DFA after digestion | 3.0 | 0.50 | — |
| 24 | propylene glycol | Add DFA after digestion | 3.0 | 0.50 | — |
| 25 | propylene glycol | 5-L scale-up preparation | 3.0 | 0.50 | — |
| 26 | 3-methyl-1,5-pentanediol | Add DFA after digestion | 3.0 | 0.50 | — |
| 27 | 3-methyl-1,5-pentanediol | Add DFA and phthalic anhydride after digestion | 2.0 | 0.25 | 0.25 |
| 28 | 2-methyl-1,3-propanediol | Add DFA after digestion | 3.0 | 0.50 | — |
| 29 | 2-methyl-1,3-propanediol | Add DFA and phthalic anhydride after digestion | 2.0 | 0.25 | 0.25 |
| 30 | propylene glycol | 5-L scale-up preparation | 3.0 | 0.50 | — |
| 31 | propylene glycol | Add DFA after digestion | 3.0 | 0.65 | — |
| 32 | propylene glycol | Add DFA after digestion; no catalyst used | 2.8 | 0.46 | — |
| 33 | propylene glycol | Add DFA after digestion; 500 ppm Ti(OBu)4 used | 2.8 | 0.46 | — |
| 34 | propylene glycol | Add DFA after digestion; 1000 ppm Ti(OBu)4 used | 2.8 | 0.46 | — |

TABLE 2

Dimer Fatty Acid-Modified Polyol Properties: Inventive Examples

| Ex | glycol/rPET (mol/mol) | DFA/rPET (mol/mol) | DA/rPET (mol/mol) | Recycle content % | Acid # (mg KOH/g) | OH # (mg KOH/g) | Color | Clarity | Settling | Visc., 25° C. |
|---|---|---|---|---|---|---|---|---|---|---|
| 1 | 3.0 | 0.50 | — | 25.6 | 4.1 | 357 | yel-amber | transp. | — | 3517 |
| 2 | 3.0 | 0.50 | — | 25.6 | 4.9 | 318 | amber | transp. | — | 3787 |
| 3 | 6.0 | 0.50 | — | 69.2 | 3.3 | 614 | yel-amber | transp. | slight | 751 |
| 4 | 6.0 | 0.50 | — | 69.2 | 5.4 | 612 | grey-yel | opaque | heavy | 840 |
| 5 | 9.0 | 0.50 | — | 75.2 | 4.4 | 791 | grey-green | opaque | heavy | 385 |
| 6 | 4.0 | 0.50 | — | 63.2 | 4.1 | 439 | lt. amber | transp. | slight | 1579 |
| 7 | 6.0 | 0.50 | — | 69.2 | 1.2 | 612 | lt. amber | sl. transp. | yes | 687 |
| 8 | 3.0 | 0.50 | — | 59.3 | 5.3 | 376 | dk. amber | sl. transp. | slight | 3097 |
| 9 | 3.0 | 0.25 | — | 74.2 | 6.3 | 522 | yel-amber | sl. transp. | slight | 1833 |
| 10 | 3.0 | 0.125 | — | 84.9 | 2.5 | 619 | yel-amber | sl. transp. | slight | 1291 |
| 11 | 3.0 | 0.25 | — | 74.2 | 4.8 | 502 | amber | sl. transp. | slight | 1901 |
| 12 | 3.0 | 0.25 | — | 74.2 | 4.6 | 510 | amber | sl. transp. | slight | 1878 |
| 13 | 3.0 | 0.25 | 0.25 | 72.3 | 2.4 | 466 | green-amber | opaque | slight | 2121 |
| 14 | 2.0 | 0.25 | — | 70.2 | 4.2 | 354 | yellow | opaque | yes | 7284 |
| 15 | 3.0 | 0.375 | 0.125 | 64.4 | 18.6 | 409 | amber | opaque | slight | 2340 |
| 16 | 2.0 | 0.20 | — | 74.5 | 3.5 | 363 | yel-amber | opaque | heavy | 7877 |
| 17 | 3.0 | 0.40 | — | 64.5 | 1.9 | 379 | amber | opaque | slight | 3994 |
| 18 | 3.0 | 0.50 | — | 59.3 | 3.8 | 382 | green | transp. | none | 3408 |
| 19 | 3.0 | 0.50 | — | 54.0 | 1.4 | 331 | yellow | opaque | none | 14,097 |
| 20 | 3.0 | 0.50 | — | 59.3 | 2.6 | 381 | green | transp. | none | 3091 |
| 21 | 3.0 | 0.50 | — | 59.3 | 5.4 | 384 | grey-green | transp. | none | 3143 |
| 22 | 3.0 | 0.50 | — | 59.3 | 9.9 | 392 | yellow | transp. | none | 2494 |
| 23 | 3.0 | 0.50 | — | 59.3 | 10.9 | 400 | amber | transp. | slight | 2642 |
| 24 | 3.0 | 0.50 | — | 59.3 | 9.2 | 392 | yellow | transp. | none | 2765 |
| 25 | 3.0 | 0.50 | — | 59.5 | 12.6 | 388 | amber | sl. transp. | none | 2805 |
| 26 | 3.0 | 0.50 | — | 23.0 | 2.8 | 300 | amber | transp. | none | 2214 |
| 27 | 2.0 | 0.25 | 0.25 | 31.4 | 3.8 | 279 | green-amber | opaque | slight | 5710 |
| 28 | 3.0 | 0.50 | — | 25.6 | 1.4 | 345 | amber | opaque | none | 4157 |
| 29 | 2.0 | 0.25 | 0.25 | 34.6 | 2.7 | 305 | amber | opaque | none | 11,790 |
| 30 | 3.0 | 0.50 | — | 59.3 | 18.1 | 363 | amber | sl. transp. | none | 3047 |

TABLE 2-continued

Dimer Fatty Acid-Modified Polyol Properties: Inventive Examples

| Ex | glycol/rPET (mol/mol) | DFA/rPET (mol/mol) | DA/rPET (mol/mol) | Recycle content % | Acid # (mg KOH/g) | OH # (mg KOH/g) | Color | Clarity | Settling | Visc., 25° C. |
|---|---|---|---|---|---|---|---|---|---|---|
| 31 | 3.0 | 0.65 | — | 54.9 | 15.1 | 282 | amber | sl. transl. | none | 5610 |
| 32 | 2.8 | 0.46 | — | 60.7 | 13.5 | 358 | golden | opaque | none | 3429 |
| 33 | 2.8 | 0.46 | — | 60.7 | 6.6 | 387 | amber | transp. | none | 3197 |
| 34 | 2.8 | 0.46 | — | 60.6 | 10.0 | 382 | amber | transp. | none | 3061 |

TABLE 3

Comparative Examples

| Ex | glycol(s) | description | glycol/rPET (mol/mol) | DFA/rPET (mol/mol) | DA/rPET (mol/mol) |
|---|---|---|---|---|---|
| C35 | propylene glycol | Add DFA after digestion | 1.5 | 0.5 | — |
| C36 | 2-methyl-1,3-propanediol | Add DFA after digestion | 1.0 | 0.5 | — |
| C37 | 2-methyl-1,3-propanediol | Add DFA after digestion | 0.75 | 0.5 | — |
| C38 | propylene glycol | Adipic acid added at the outset, uncatalyzed | 2.0 | — | 1.0 |
| C39 | propylene glycol | Succinic acid added at the outset, uncatalyzed | 2.0 | — | 1.0 |
| C40 | propylene glycol | Add succinic acid after digestion, catalyzed | 2.0 | — | 1.0 |
| C41 | propylene glycol | Add succinic acid after digestion, catalyzed | 6.0 | — | 0.5 |
| C42 | propylene glycol | Add succinic acid after digestion, catalyzed | 9.0 | — | 0.5 |
| C43 | 2-methyl-1,3-propanediol | Add DFA after digestion | 1.0 | 0.5 | — |
| C44 | propylene glycol | Add phthalic anhydride after digestion | 0.9 | — | 0.2 |
| C45 | propylene glycol | Add dibasic acid mixture after digestion | 2.0 | — | 1.0 |
| C46 | propylene glycol | Use Texaco procedure with DBA; use PG instead of DEG | 2.0 | — | 1.0 |
| C47 | propylene glycol | Control: rPET digestion with no DFA or diacid | 3.0 | — | — |
| C48 | propylene glycol | Control: rPET digestion with no DFA or diacid | 4.0 | — | — |
| C49 | diethylene glycol | Add DBA after digestion | 2.0 | — | 1.0 |
| C50 | 3-methyl-1,5-pentanediol | Add phthalic anhydride after digestion | 2.0 | — | 0.5 |
| C51 | 2-methyl-1,3-propanediol | Add phthalic anhydride after digestion | 2.0 | — | 0.5 |
| C52 | propylene glycol | Add succinic acid after digestion | 3.0 | — | 0.5 |
| C53 | propylene glycol | Add adipic acid after digestion | 3.0 | — | 0.5 |

TABLE 4

Comparative Examples

| Ex | glycol/rPET (mol/mol) | DFA/rPET (mol/mol) | DA/rPET (mol/mol) | Recycle content % | Acid # (mg KOH/g) | OH # (mg KOH/g) | Color | Clarity | Settling | Visc., 25° C. |
|---|---|---|---|---|---|---|---|---|---|---|
| C35 | 1.5 | 0.5 | — | 51.5 | 2.6 | 256 | yellow | opaque | — | 10,969 |
| C36 | 1.0 | 0.5 | — | 33.6 | 7.0 | 55 | grey green | opaque | solid | barely flows |
| C37 | 0.75 | 0.5 | — | 35.0 | 3.4 | 27 | grey-green | opaque | solid | none |
| C38 | 2.0 | — | 1.0 | 70.2 | 6.6 | 215 | white-grey | opaque | solid | 20,156 |
| C39 | 2.0 | — | 1.0 | 74.4 | 5.8 | 236 | white-grey | opaque | solid | none |
| C40 | 2.0 | — | 1.0 | 73.9 | 11.1 | 326 | grey-green | opaque | none | 62,487 |
| C41 | 6.0 | — | 0.5 | 91.1 | 1.1 | 882 | grey-green | opaque | yes | 253 |
| C42 | 9.0 | — | 0.5 | 93.3 | 1.2 | 1022 | grey | opaque | yes | 144 |
| C43 | 1.0 | 0.5 | — | 22.4 | 28.9 | — | grey-amber | opaque | none | barely flows |
| C44 | 0.9 | — | 0.2 | 89.2 | 30.7 | 322 | tan-grey | opaque | — | none |
| C45 | 2.0 | — | 1.0 | 84.8 | 25.5 | 241 | grey-amber | opaque | none | 26,889 |
| C46 | 2.0 | — | 1.0 | 85.6 | 12.0 | 191 | white-grey | opaque | solid | none |
| C47 | 3.0 | — | — | 99.1 | 2.0 | 730 | brown | opaque | slight | 652 |
| C48 | 4.0 | — | — | 99.3 | 1.8 | 860 | green-amber | sl. transp. | slight | 345 |
| C49 | 2.0 | — | 1.0 | 41.6 | 7.3 | 217 | white-grey | opaque | none | 7056 |
| C50 | 2.0 | — | 0.5 | 37.9 | 5.1 | 223 | grey | opaque | slight | 13,497 |
| C51 | 2.0 | — | 0.5 | 42.7 | 10.2 | 349 | green-amber | opaque | none | 35,492 |
| C52 | 3.0 | — | 0.5 | 87.0 | 1.3 | 572 | tan-green | opaque | slight | 1250 |
| C53 | 3.0 | — | 0.5 | 84.6 | 21.3 | 566 | tan-green | opaque | slight | 1167 |

Settling Experiment

The polyurethane dispersion prepared above is filtered through a 190-μm paint filter and into a settling cone. The cone is sealed with Parafilm® "M" laboratory film and stored for 19 days in a dark cabinet. After the settling period is concluded, the dispersion shows no apparent settling (~0.0 mL).

A similar polyurethane dispersion prepared from a glycol-digested recycled polyethylene terephthalate (0.9 propylene glycol to 1 rPET) and not modified with dimer fatty acid has 0.4 mL of settled material after 19 days.

Acrylate From DFA-Modified Polyol

A flask equipped with addition funnel, condenser, heating mantle, thermocouple, and mechanical stirring is charged with a dimer fatty acid-modified polyol (75.0 g, produced as described above from recycled polyethylene terephthalate (28.3 wt. %), propylene glycol (31.4 wt. %), titanium(IV) butoxide (0.5 wt. %), and Pripol™ 1017 dimer fatty acid (39.8 wt. %)), tetrahydrofuran (300 mL), triethylamine (50.8 g), and phenothiazine (0.19 g). The stirred mixture is heated to 50° C. The resulting solution is cooled to 10° C., and acryloyl chloride (44.8 g) is added over 2 h. Stirring continues for an additional 1 h. The resulting product is filtered through Celite® 545 filter aid to remove precipitated triethylamine hydrochloride. The filtrate is stripped under vacuum and redissolved in dichloromethane (350 mL). The organic phase is washed with 10% aq. NaOH solution, then with 10% aq. NaCl solution, then dried (MgSO$_4$) and concentrated (40-60° C., 70 mm Hg). Yield: 84.6 g. Analysis by $^1$H NMR spectroscopy shows that conversion to the acrylate ester is complete.

Acrylate Coatings

Coatings are produced using the DFA-modified polyol acrylate described above and a control formulation. The control formulation (50 wt. % solids in methyl ethyl ketone (MEK)) is prepared from bisphenol A ethoxylate diacrylate (66.5 wt. %), ethylene glycol phenyl ether acrylate (26.5 wt. %), Addox™ A40 adhesion promoter (5.0 wt. %, product of Doxa Chemical), and Irgacure® 1173 photoinitiator (2.0 wt. %, product of BASF). The DFA-modified polyol acrylate formulation (50 wt. % solids in MEK) is prepared from bisphenol A ethoxylate diacrylate (37.1 wt. %), ethylene glycol phenyl ether acrylate (15.9 wt. %), DFA modified polyol acrylate (40 wt. %, prepared as described above), Addox™ A40 adhesion promoter (5.0 wt. %), and Irgacure® 1173 photoinitiator (2.0 wt. %). Films are drawn down to provide cured coatings having an average film thickness of 1.6-1.8 mils. The coatings are cured with four passes of a Jelight handheld UV curing lamp followed by one pass on a UV bench top conveyor unit (Heraeus Noblelight) running at 5 ft./min. Results appear in Table 5.

Testing Methods for Acrylate Coatings:

Dry film thickness is determined using a PosiTector 6000 (Defelsko Corporation) dry film thickness gauge. Konig hardness is measured using ISO 1522 using a TOC pendulum hardness tester (Model SPO500). The following ASTM test methods are used: pencil hardness: ASTM D3363; flexibility: ASTM D522; adhesion: ASTM 03359; stain testing: ASTM 01308.

TABLE 5

Acrylate Coating Results

|  | Control | DFA-modifed polyol acrylate |
|---|---|---|
| Film thickness (mil) | 1.64 | 1.74 |
| Konig hardness (s) | 206 | 151 |
| Pencil hardness | 2H | 2H |
| Cross-hatch adhesion | 5B | 6B |
| Mandrel bend 1", ⅝", ⅛" | P, P, P | P, P, P |
| MEK double rubs | >200 | >200 |
| Stain testing |  |  |
| Methyl ethyl ketone (1 h) | 5 | 5 |
| Isopropyl alcohol (1 h) | 5 | 5 |
| Mustard (1 h) | 5 | 5 |
| Windex ® cleaner (24 h) | 4 | 5 |
| Vinegar (24 h) | 4 | 5 |
| Water (24 h) | 4 | 5 |
| Water soak test (3 h; hardness, value) | 4H, 1F | <H, 1F |

Rigid Foam From Dimer Fatty Acid-Modified Polyester Polyol

"Part B" components are combined in a large plastic beaker (6" diameter, 5" tall) by mixing until homogeneous a dimer fatty acid-based polyol (mol. wt. 500, hydroxyl value=224 mg KOH/g, 70.4 wt. %, prepared from recycled PET (28.7 wt. %), propylene glycol (31.9 wt. %), dimer fatty acid (39.3 wt. %) and titanium(IV) butoxide (0.10 wt. %) as described previously) with Fyrol™ PCF flame retardant (8.0 wt. %, product of Israel Chemical Ltd.), Dabco® K-15 catalyst (1.60 wt. %, Air Products), Polycat® 5 catalyst (0.13 wt. %, Air Products), Tegostab® B8465 silicone surfactant (2.6 wt. %, Evonik), water (0.32 wt. %), and n-pentane (18.3 wt. %). These percentages are based on the amount of Part B component.

"Part A," comprised of PAPI™ 27 isocyanate (polymeric MDI, 53.3 wt. % based on the combined amounts of Parts A and B, 260 NCO/OH index, product of Dow Chemical), is then quickly added. Immediately after addition of Part A to Part B, the container is placed on a VOS power control mixer (VWR International) equipped with 3-inch diameter Cowles blade and mixed at up to 2000 RPM for ten seconds. The mixing time is controlled by an electronic timer with foot pedal attachment (GraLab Model 451). Immediately after mixing stops, the well-mixed foam is poured into a 12"×12"×12" cardboard box and allowed to rise. After fully curing under ambient conditions, the foam is tested for compressive strength (ASTM D1621) and thermal conductivity (ASTM C177).

The preceding examples are meant only as illustrations; the following claims define the inventive subject matter.

We claim:

1. A polyester polyol comprising recurring units of a glycol-digested polyethylene terephthalate (PET) or glycol-modified polyethylene terephthalate (PETG) and an unsaturated dimer fatty acid, wherein the glycol is selected from the group consisting of propylene glycol, diethylene glycol, and 2-methyl-1,3-propanediol, the molar ratio of dimer fatty acid to PET or PETG is within the range of 0.1 to 0.5, the molar ratio of glycol to PET or PETG is within the range of 2.5 to 4.5, and the polyol has a hydroxyl number within the range of 40 to 400 mg KOH/g.

2. The polyol of claim 1 wherein the PET is selected from the group consisting of virgin PET, recycled PET, and mixtures thereof.

3. The polyol of claim 1 wherein the glycol comprises a recycled glycol.

4. The polyol of claim 1 having a hydroxyl number within the range of 200 to 400 mg KOH/g.

5. The polyol of claim 1 having a viscosity at 25° C. less than 10,000 cP.

6. A transparent polyol of claim 1.

7. The polyol of claim 1 having a recycle content as defined herein greater than 50 wt. %.

8. The polyol of claim 1 wherein the unsaturated dimer fatty acid comprises dimerized oleic acid, trimerized oleic acid, dimerized linoleic acid, trimerized linoleic acid, dimerized linolenic acid, trimerized linolenic acid, or mixtures thereof.

9. The polyol of claim 1 having an acid number of less than 10 mg KOH/g.

10. The polyol of claim 1 wherein the molar ratio of dimer fatty acid to PET or PETG is within the range of 0.2 to 0.5.

11. A polyester polyol comprising recurring units of a glycol-digested polyethylene terephthalate (PET) or glycol-modified polyethylene terephthalate (PETG) and an unsaturated dimer fatty acid, wherein the glycol is selected from the group consisting of sorbitol, neopentyl glycol, glycerol, 2,2,4,4-tetramethyl-1,3-cyclobutanediol, 3-methyl-1,5-pentanediol, 1,4-cyclohexanedimethanol, 1,3-cyclohexanedimethanol, bisphenol A ethoxylates, 1,6-hexanediol, block or random copolymers of ethylene oxide and propylene oxide, and mixtures thereof, the molar ratio of dimer fatty acid to PET or PETG is within the range of 0.1 to 0.5, the molar ratio of glycol to PET or PETG is within the range of 2.5 to 4.5, and the polyol has a hydroxyl number within the range of 40 to 400 mg KOH/g.

12. The polyol of claim 11 wherein the PET is selected from the group consisting of virgin PET, recycled PET, and mixtures thereof.

13. The polyol of claim 11 wherein the glycol comprises a recycled glycol.

14. The polyester polyol of claim 11 having a hydroxyl number within the range of 200 to 400 mg KOH/g.

15. The polyester polyol of claim 11 wherein the molar ratio of dimer fatty acid to PET or PETG is within the range of 0.2 to 0.5.

16. The polyol of claim 11 having a viscosity at 25° C. less than 10,000 cP.

17. A transparent polyol of claim 11.

18. The polyol of claim 11 having a recycle content as defined herein greater than 50 wt. %.

19. The polyol of claim 11 wherein the unsaturated dimer fatty acid comprises dimerized oleic acid, trimerized oleic acid, dimerized linoleic acid, trimerized linoleic acid, dimerized linolenic acid, trimerized linolenic acid, or mixtures thereof.

20. The polyol of claim 11 having an acid number of less than 10 mg KOH/g.

\* \* \* \* \*